US006951544B2

(12) United States Patent
Trahey et al.

(10) Patent No.: US 6,951,544 B2
(45) Date of Patent: Oct. 4, 2005

(54) METHOD AND APPARATUS FOR THE IDENTIFICATION AND CHARACTERIZATION OF REGIONS OF ALTERED STIFFNESS

(75) Inventors: Gregg E. Trahey, Hillsborough, NC (US); Kathryn R. Nightingale, Durham, NC (US); Roger W. Nightingale, Durham, NC (US); Mark Palmeri, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 10/240,909

(22) PCT Filed: Apr. 5, 2001

(86) PCT No.: PCT/US01/11051

§ 371 (c)(1),
(2), (4) Date: Feb. 26, 2003

(87) PCT Pub. No.: WO01/76484

PCT Pub. Date: Oct. 18, 2001

(65) Prior Publication Data

US 2003/0171676 A1 Sep. 11, 2003

Related U.S. Application Data

(63) Continuation of application No. 09/663,271, filed on Sep. 18, 2000, now Pat. No. 6,371,912.
(60) Provisional application No. 60/194,746, filed on Apr. 5, 2000.

(51) Int. Cl.[7] .............................................. A61B 8/06

(52) U.S. Cl. ..................................................... 600/449

(58) Field of Search ................................. 600/437–472; 128/916; 367/7, 11, 130, 138; 73/595–633

(56) References Cited

U.S. PATENT DOCUMENTS

| 4,913,157 A | 4/1990 | Pratt, Jr. et al. ......... 128/661.03 |
| 5,099,848 A | 3/1992 | Parker et al. .......... 128/661.07 |
| 5,107,837 A | 4/1992 | Ophir et al. ........... 128/660.01 |
| 5,487,387 A | 1/1996 | Trahey et al. .......... 128/660.02 |
| 5,524,636 A | 6/1996 | Sarvazyan et al. .......... 128/774 |
| 5,810,731 A | 9/1998 | Sarvazyan et al. .......... 600/438 |
| 5,921,928 A | 7/1999 | Greenleaf et al. .......... 600/437 |
| 6,371,912 B1 * | 4/2002 | Nightingale et al. ........ 600/437 |

FOREIGN PATENT DOCUMENTS

WO        98/55025        12/1998

OTHER PUBLICATIONS

A. Saravazyan et al., Biophysical Bases of Elasticity Imaging, *Acoustic Imaging* 21, 223–240 (1995).

K. Nightingale, *Ultrasonic Generation and Detection of Acoustic Streaming to Differentiate Between Fluid–Filled and Solid Lesions in the Breast* (Ph.D. Thesis, Duke University, Sep. 1997).

(Continued)

*Primary Examiner*—Ali Imam
(74) *Attorney, Agent, or Firm*—Myers Bigel Sibley & Sajovec

(57) ABSTRACT

A remote palpation technique in breast imaging involves the use of multiple applications of radiation force in rapid succession throughout a two-dimensional plane in the target tissue medium (10), and combination of the small, two-dimensional displacement maps from each force location into a single, larger remote palpation image (block 43). Apparatus for carrying out the foregoing method is also disclosed.

35 Claims, 4 Drawing Sheets

OTHER PUBLICATIONS k. Nightingale, R. Nightingale, T. Hall, and G. Trahey, The use of radiation force induced tissue displacements to image stiffness: a feasibility study, 23$^{rd}$ International Symposium on Ultrasonic Imaging and Tissue Characterization, May 27–29, 1998.

Krouskop et. al., Elastic Moduli of Breast and Prostate Tissues Under Compression, *Ultrasonic Imaging* 20, 260–274 (1998).

M. Fatemi and J. Greenleaf, Ultrasound–stimulated vibro–acoustic spectrography, *Science*, 280:82–85, (1998).

K.R. Nightingale, R.W. Nightingale, M.L. Palmeri, and G.E. Trahey, Finite element analysis of radiation force induced tissue motion with experimental validatiion, In *Proceedings of the 1999 IEEE Ultrasonics Symposium*, page in press, 1999.

K. Nightingale et al., Utilization of Acoustic Streaming to Classify Breast Lesions in Vivo, *Proceedings of the 1997 IEEE Ultrasonics Symposium*, 1419–1422 (Toronto, CA, Oct. 1997).

A. Sarvazyan, O. Rudenko, S. Swanson, J. Fowlkes, and S. Emelianov, Shear wave elasticity imaging: A new ultrasonic technology of medical diagnostics,*Ultrasound Med. Biol.* 24:9 1419–1435 (1998).

T. Sugimoto, S. Ueha, and K. Itoh, Tissue hardness measurement using the radiation force of focused ultrasound, In *Proceedings of the 1990 Ultrasonics Symposium*, pp. 1377–1380, 1990.

W. Walker, Internal deformation of a uniform elastic solid by acoustic radiation force,*J. Acoust. Soc. Am.,* 105: 4 2508–2518 (1999).

Supplementary Partial European Search Report for EP Application 01 93 0447 dated Feb. 2, 2005.

International Search Report; PCT/US01/11051; filed Apr. 5, 2001.

* cited by examiner

METHOD AND APPARATUS FOR THE IDENTIFICATION AND CHARACTERIZATION OF REGIONS OF ALTERED STIFFNESS

RELATED APPLICATIONS

This application claims priority from International PCT Application No. US01/11051, filed Apr. 5, 2001 and is a continuation of U.S. application Ser. No. 09/663,271, filed Sep. 18, 2000, now U.S. Pat. No, 6,371,912, which claimed the benefit of U.S. Provisional Application Ser. No. 60/194,746, filed Apr. 5, 2000, the disclosures of which are incorporated by reference herein in their entireties.

GOVERNMENT SUPPORT

This invention was made with Government support under grant number DAMD17-98-1-8068 from the Department of Defense. The Government has certain rights to this invention.

FIELD OF THE INVENTION

The present invention concerns ultrasound methods and apparatus for the identification and characterization of regions of altered stiffness in a target media.

BACKGROUND OF THE INVENTION

The early detection of breast cancer has been shown to significantly improve patient survival. Present methods of breast cancer detection include screening mammography and palpation, either by patient self-examination or clinical breast exam. Palpation relies on the manual detection of differences in tissue stiffness between breast lesions and normal breast tissue. The success of palpation is due to the fact that the elastic modulus (or Young's modulus) of malignant tumors is often an order of magnitude greater than that of normal breast tissue. That is, cancerous lesions feel "hard" or "stiff" as compared to normal breast tissue. See T. Krouskop et al., *Ultrasonic Imaging* 20, 260–274 (1998); A. Saravazyan et al., *Acoustic Imaging* 21, 223–240 (1995).

Recently, the use of ultrasonic radiation force to remotely characerize tissue stiffness has been proposed. One particular approach is referred to as remote palpation. In remote palpation, acoustic radiation force is used to apply localized forces within tissue, and the resulting tissue displacements are mapped using either ultrasonic correlation based methods, or other pattern matching methods. A volume of tissue that is stiffer than the surrounding medium (i.e., a lesion) may distribute the force throughout the tissue beneath it, resulting in larger regions of displacement, and smaller maximum displacements. Remote palpation is described in K. Nightingale, *Ultrasonic Generation and Detection of Acoustic Streaming to Differentiate Between Fluid-Filled and Solid Lesions in the Breast* (Ph.D. Thesis, Duke University, September 1997), and in K Nightingale et al., *Proceedings of the 1997 IEEE Ultrasonics Symposium*, 1419–1422 (Toronto, Calif., October 1997).

U.S. Pat. No. 5,921,928 to Greenleaf uses sound and sonic waves to vibrate tissue and monitors the sound of the vibrating tissue. A disadvantage of such am approach is that different transmit and detection systems may be required, and multiple pushing cycles at a single location may be required.

Remote palpation has not yet been implemented in a form feasible for actual clinical diagnosis. Accordingly, there remains a need for new methods and systems to implement remote palpation.

SUMMARY OF THE INVENTION

The present invention is based upon the finding that an improved implementation of remote palpation in breast imaging can involve the use of multiple applications of radiation force in rapid succession throughout a two-dimensional plane in the target tissue, and the combination of the small, two-dimensional displacement maps from each force location into a single, larger remote palpation image. The use of multiple forcing locations may present a significant improvement in the remote palpation method, in that it may facilitate real-time, implementation of the method, which can allow more thorough interrogation of a suspicious region of tissue, as well as correlation and superposition of remote palpation images and conventional B-mode images. It may also reduce or even obviate the need for bulky, complex external fixtures during implementation of the method.

DETAILED DESCRIPTION OF THE PREFERRED EMBODIMENTS

While the present invention may be used to detect regions of varying stiffness (i.e., increased or decreased elastic modulus) in any type of medium, the medium is in a preferred embodiment a biological tissue such as breast tissue in a living subject, where the regions of varying stiffness to be detected are tumors.

The invention may be carried out on human subjects for diagnostic or prognostic purposes, and may be carried out on animal subjects such as dogs and cats for veterinary purposes.

Circuits and devices described herein may be implemented as general or special purpose hardware devices, as software running on or programmed into general or special purpose hardware devices, or as combinations thereof.

Numerous variations and implementations of the instant invention will be apparent to those skilled in the art. Ultrasound apparatus is known, and is described in, for example, U.S. Pat. No. 5,487,387 to Trahey et al.; U.S. Pat. No. 5,810,731 to Sarvazyan and Rudenko; U.S. Pat. No. 5,921,928 to Greenleaf et al.; M. Fatemi and J. Greenleaf, Ultrasound-stimulated vibro-acoustic spectrography, *Science*, 280:82–85, (1998); K. Nightingale, *Ultrasonic Generation and Detection of Acoustic Streaming to Differentiate Between Fluid-Filled and Solid Lesions in the Breast*, Ph.D. thesis, Duke University, 1997; K. Nightingale, R. Nightingale, T. Hall, and G. Trahey, The use of radiation force induced tissue displacements to image stiffness: a feasibility study, $23^{rd}$ International Symposium on Ultrasonic Imaging and Tissue Characterization, May 27–29, 1998; K. R. Nightingale, P. J. Kornguth, S. M. Breit, S. N. Liu, and G. E. Trahey, Utilization of acou vivo, In *Proceedings of the 1997 IEEE Ultrasonics Symposium*, pages 1419–1422, 1997; K. R. Nightingale, R. W. Nightingale, M. L. Palmeri, and G. E. Trahey, Finite element analysis of radiation force induced tissue motion with experimental validation, In *Proceedings of the 1999 IEEE Ultrasonics Symposium, page in press,* 1999; A. Sarvazyan, O. Rudenko, S. Swanson, J. Fowlkes, and S. Emelianov, Shear wave elasticity imaging: A new ultrasonic technology of medical diagnostics, *Ultrasound Med. Biol.* 24:9 1419–1435 (1998); T. Sugimoto, S. Ueha, and K. Itoh, Tissue hardness measurement using the radiation force of focused ultrasound, In *Proceedings of the 1990 Ultrasonics Symposium*, pages 1377–1380, 1990; and W. Walker, Internal deformation of a uniform elastic solid by acoustic radiation force, *J. Acoust. Soc. Am.,* 105:4 2508–2518 (1999). The disclosures of these references are to be incorporated herein by reference in their entirety for their teaching of various elements and features that may be used to implement and carry out the invention described herein.

Figure 1:
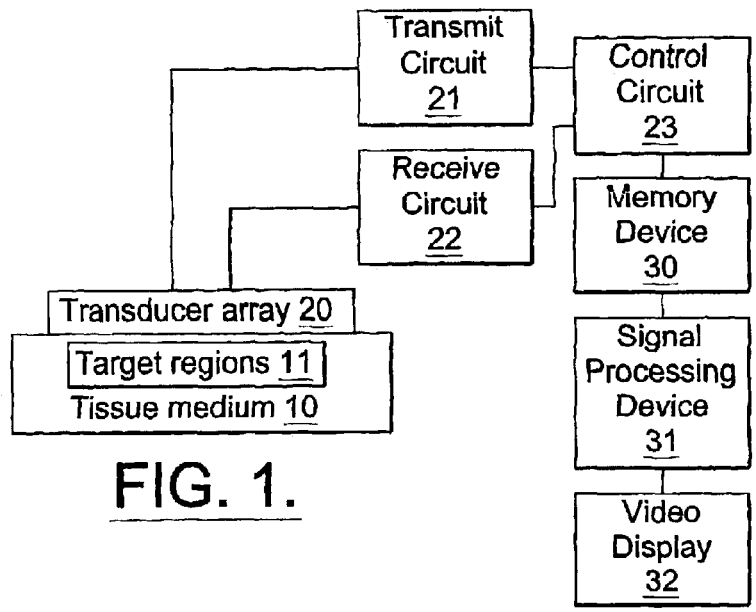
FIG. 1 is a block diagram illustrating embodiments of an apparatus that may be used to carry out the present invention.

An illustrative example of an apparatus of the invention is given in FIG. 1. The apparatus comprises an ultrasound transducer array 20, which may be a one-dimensional array or a two-dimensional array, which is contacted to a target medium, typically a tissue medium 10. The array is directed to a two-dimensional plane comprising one or more, and preferably a plurality of, target regions 11 within the tissue medium. A transmit circuit 21 is operatively associated with the transducer array and delivers high energy "pushing" pulses to a forcing region among the target regions (i.e., pulses that can induce a physical displacement of the tissue within the target regions), as well as for delivering relatively lower energy "tracking" pulses. A receive circuit 22 is connected to the transducer array 20 to receive information from the target regions 11 for subsequent signal processing. The transmit circuit 21 and detector circuit 22 are both operatively associated with an appropriate control circuit 23 that triggers the pushing pulses and tracking pulses, organizing information received from the target regions for subsequent signal processing, and which also cycles the pushing pulses and corresponding tracking pulses through different forcing regions.

Information received by receive circuit 22 can be stored in a memory device 30 such as a random access memory or other suitable memory device, which serves as a means for storing both initial and displaced positions of target regions. A signal processing device or signal processor 31 is operatively associated with the memory device 30, and serves as a means for generating initial images for particular forced regions and a single combined image for a plurality of forced regions.

A method of the present invention may comprise the steps of:

(a) delivering a set of tracking pulses from a plurality of transducer elements in an ultrasound transducer array to one or a plurality of target regions in a two-dimensional plane within said medium to detect an initial positions for said one or plurality of target regions;

(b) storing said initial positions for said one or plurality of target regions; then (c) delivering a first set of pushing pulses from said plurality of transducer elements to a forcing region among said target regions to displace said target regions to subsequent (e.g., displaced) positions;

(d) delivering a second set of tracking pulses from said plurality of transducer elements in said ultrasound transducer array to said one or plurality of target regions to detect subsequent positions for said one or plurality of target regions, (e) storing said displaced positions for said one or plurality of target regions;

(f) repeating steps (a) through (e) in a series of cycles, with said pushing and tracking pulses being delivered from a different plurality of transducer elements or the same plurality of transducer elements in said array to a different forcing region, and preferably to a plurality of different target regions, during each of said cycles;

(g) generating a two-dimensional displacement map from each of said initial positions and displaced positions for each of said forcing regions to produce a plurality of two-dimensional displacement maps; and then (h) combining said plurality of two-dimensional displacement maps into a single combined image, with a region of increased stiffness being indicated by a region of decreased displacement within said combined image, or a region of decreased stiffness being indicated by a region of increased displacement within said combined image.

Step (d) above may optionally be carried out while concurrently delivering an interspersed set of pushing pulses to said forcing region to reduce the return of said target regions from said displaced positions to said initial positions.

Steps (a) through (e) above are preferably completed in a total of 50, 25 or 10 milliseconds or less for each cycle (i.e., each forced region). Preferably, a cycle of steps (a) through (d) can be completed in 15 milliseconds or less.

In one embodiment, the pushing pulses are delivered before the first set of tracking pulses, the initial positions are displaced positions, and the second positions are relaxed positions. In another embodiment, the pushing pulses are delivered between the first and second set of pulses, the initial positions indicate the relaxed positions, and the second positions indicate the displaced positions.

Figures 2A, 2B, 2C:
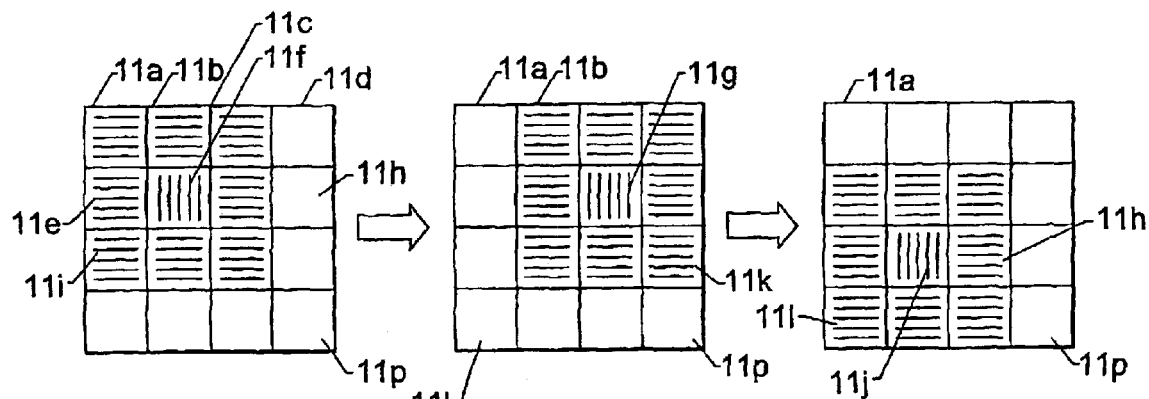
FIG. 2 illustrates the sequential scanning of the two dimensional plane of target regions of FIG. 1, with different forced regions in each cycle, to produce a two dimensional displacement map for each forced region.
Figure 5:
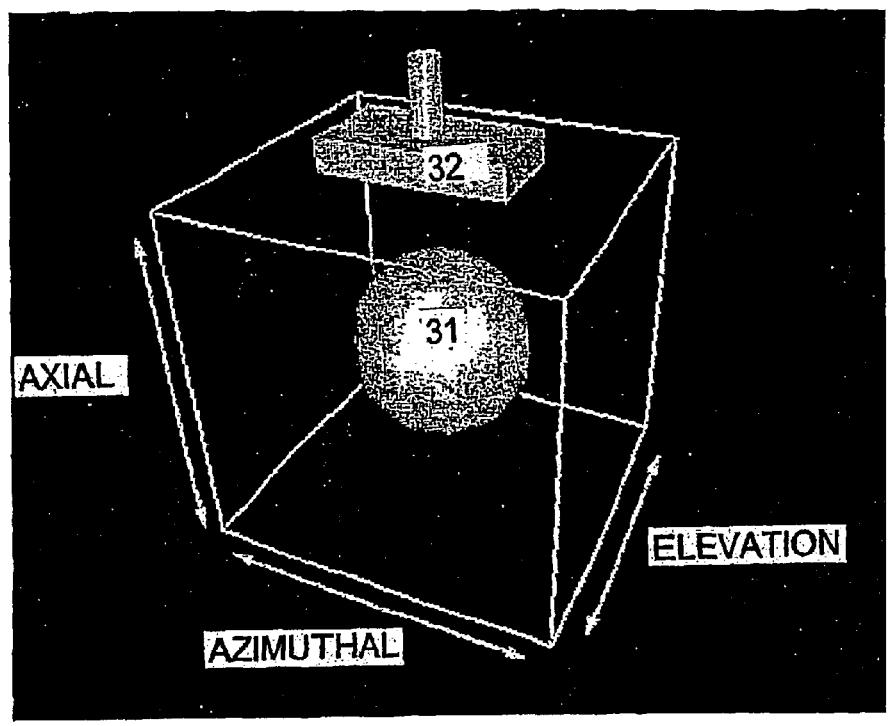
FIG. 5 illustrates embodiments of an orientation of a transducer, and the terminology associated with the different dimensions: axial, azimuthal, and elevation.

FIG. 2 illustrates the cyclic repeating of steps (a) through (e) above for different forced regions (vertical hatched regions 11*f*, 11*g*, and 11*j*) within the target regions (11*a* through 11*p*) in the axial/azimuthal plane (see FIG. 5). The Boxes represent the same view as that shown in FIG. 1. Arrows represent transition from one cycle to another (cycles A, B, and C). Note that not all target regions need be detected during each cycle, and hence the corresponding transducer elements may be active or inactive in various patterns during each cycle.

Figure 3:
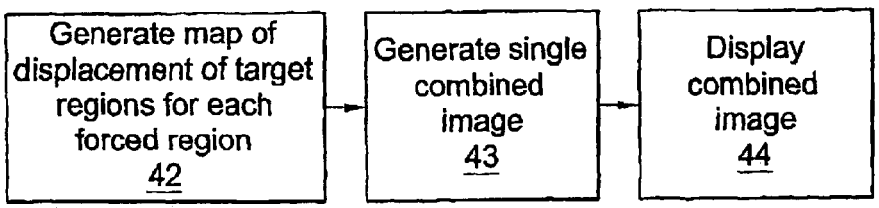
FIG. 3 illustrates the signal processing operations implemented by the signal processing device (31) of FIG. 1, in which the two dimensional displacement maps for each forced region, as generated in FIG. 2, are combined into a single image.

As shown in block 42 of FIG. 3, a two-dimensional displacement map can then be generated for each cycle A, B, and C of FIG. 2. These two-dimensional displacement maps are then used to generate a single combined image (block 43) in the signal processing device 31 of FIG. 1. This combined image can then be displayed (block 44) on the video display device 32 of FIG. 1. Of course, the single combined image may also be stored in a suitable memory device for future reference, printed on a printer, etc. The method may further comprise generating a B-mode image of the two dimensional plane in accordance with conventional techniques, and then displaying the single combined image superimposed on that B-mode image.

The invention can be implemented on a Siemens Elegra ultrasound scanner, modified to provide control of beam sequences and access to raw radio frequency data. A Siemens 75L40 transducer may be used as the transducer array.

One particular embodiment of the invention may be carried out as follows:

First, a group of low intensity "tracking lines" that interrogate the tissue surrounding the position of interest are fired and stored for tissue initial position reference.

Second, a series of one or more focused, high intensity "pushing lines" is fired along a single line of flight focused at the position of interest.

Third, the original group of tracking lines is fired again, in order to determine the relative motion caused by the radiation force associated with the pushing lines. These tracking lines may optionally be interspersed with pushing lines in order to reduce or avoid relaxation of the tissue.

Fourth, each tracking line is divided into sequential axial search regions, and the displacements of the tissue within each search region are determined. A number of different motion tracking algorithms can be used to determine the relative motion, or displacement, between the initial reference tracking lines and the second set of tracking lines fired after radiation force application. Examples include, but are not limited to, cross correlation and Sum Absolute Difference (SAD). The a priori knowledge of the direction of motion reduces the algorithm implementation time.

Steps 1–4 above are preferably accomplished in 50, 25 or 10 milliseconds or less. The results of step 4 are used to generate a two-dimensional displacement map of the region of tissue surrounding the position of interest (or force location).

Fifth, steps 1 through 4 can be repeated, cyclically, for a plurality of force locations within a larger two-dimensional imaging plane. The number of forcing locations and the spatial distribution of the forcing locations may be determined by (among other things) the specific transducer, transmit parameters, and the size of the region of interest to be interrogated. The same or different sets of elements within the transducer array may be used for the tracking pulses with each force location.

Sixth, each of the two dimensional displacement maps (each of which may be generated before, during or after subsequent cyclical repeatings of steps 1–4) can be combined into a single image (which may or may not be displayed on a video monitor, printer or other such display means). Signal processing such as averaging of collocated regions, and/or some type of normalization to account for the displacement generated in a homogeneous region of tissue, may be employed.

Note that it is also possible with certain embodiments of the invention to monitor the displacement of the tissue over time, both while the force is being applied (by interspersing the pushing lines and the tracking lines), and after cessation of the high intensity pushing lines or pulses. This is accomplished by firing the group of tracking lines repeatedly at the desired time intervals, and evaluating the changes in the displacement maps over time.

Figures 4A, 4B:
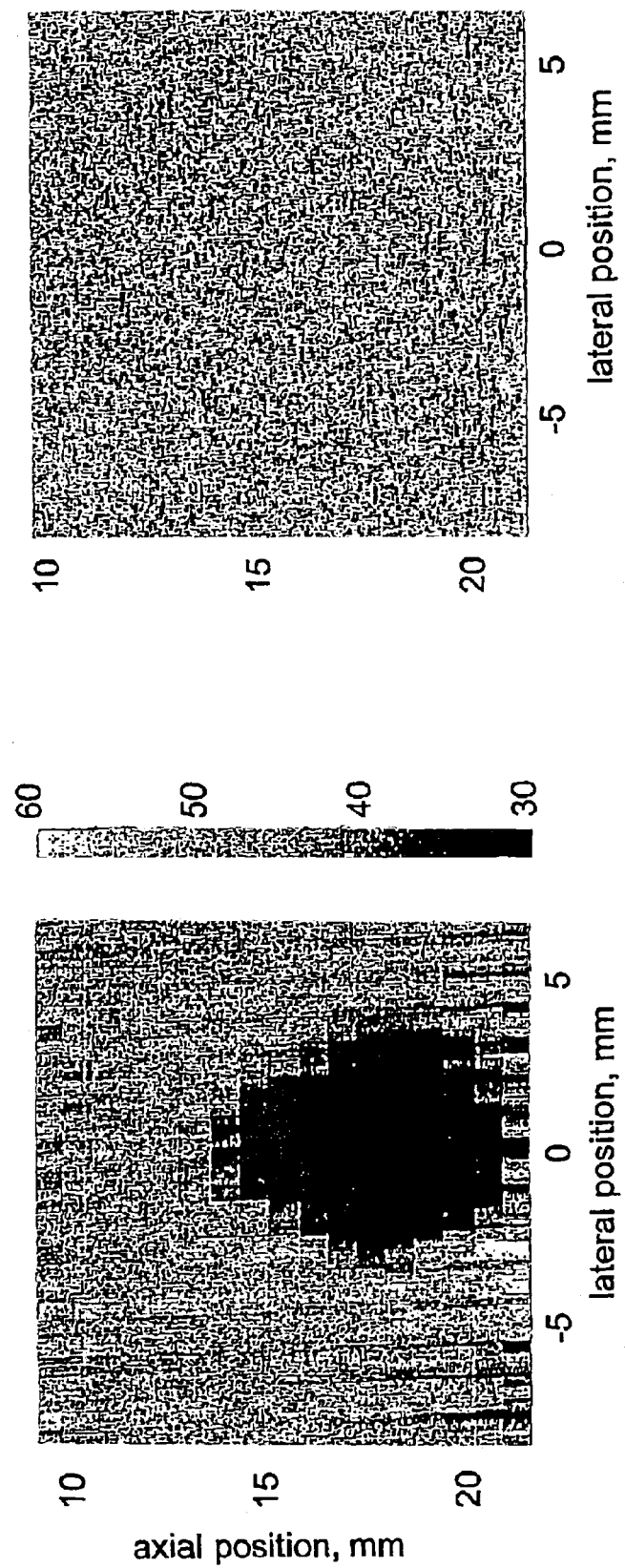
FIG. 4A, is an example remote palpation image of a breast lesion phantom.
FIG. 4B is the corresponding B-mode image of the breast lesion phantom shown in FIG. 4A.

FIG. 4A is an example remote palpation image of a breast lesion phantom. This image was generated using multiple forcing locations, separated by 1 millimeter (mm) in both the axial and azimuthal dimensions. The image spans a 9×11 mm region, for a total of 99 different pushing locations. FIG. 4B provides the corresponding B-mode image.

It has been observed that some tissues exhibit strain-stiffening behavior (i.e. glandular tissue, carcinoma) whereas other tissues do not (i.e. fatty breast tissue). Therefore, in methods intended to characterize the stiffness of tissue, it is often advantageous to pre-compress the tissue. This has the effect of increasing the contrast between the different tissue types (Krouskop et. al., Elastic Moduli of Breast and Prostate Tissues Under Compression, *Ultrasonic Imaging* 20, 260–274 (1998)). This will also be the case for the methods described herein.

Figure 6:
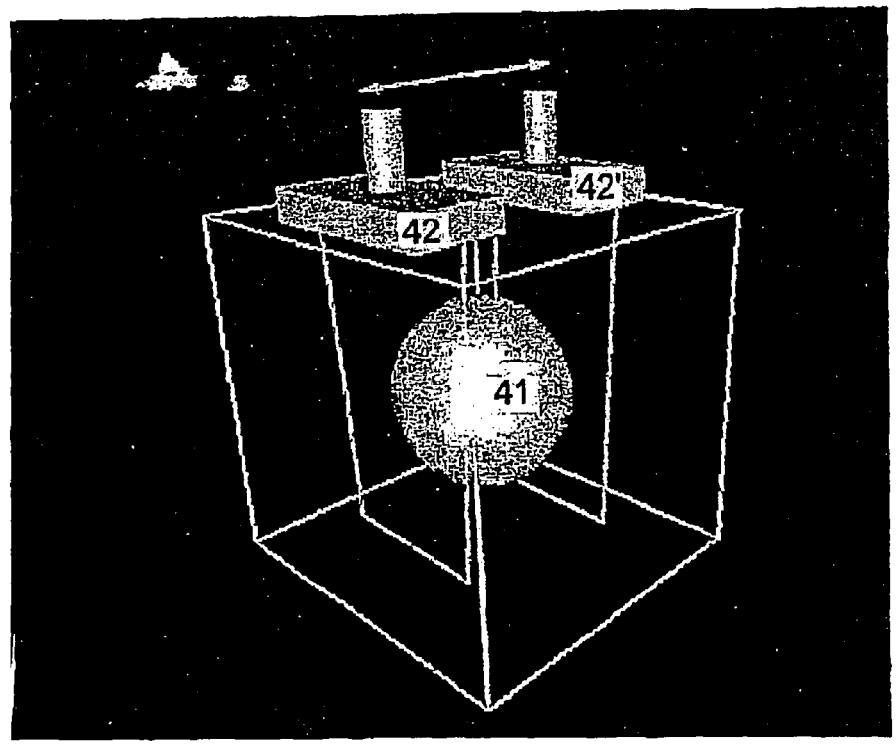
FIG. 6 illustrates embodiments of generating a three-dimensional volume using a translation stage connected to the transducer, which allows the interrogation of multiple axial/azimuthal planes by translating the transducer in the elevation dimension.
Figure 7:
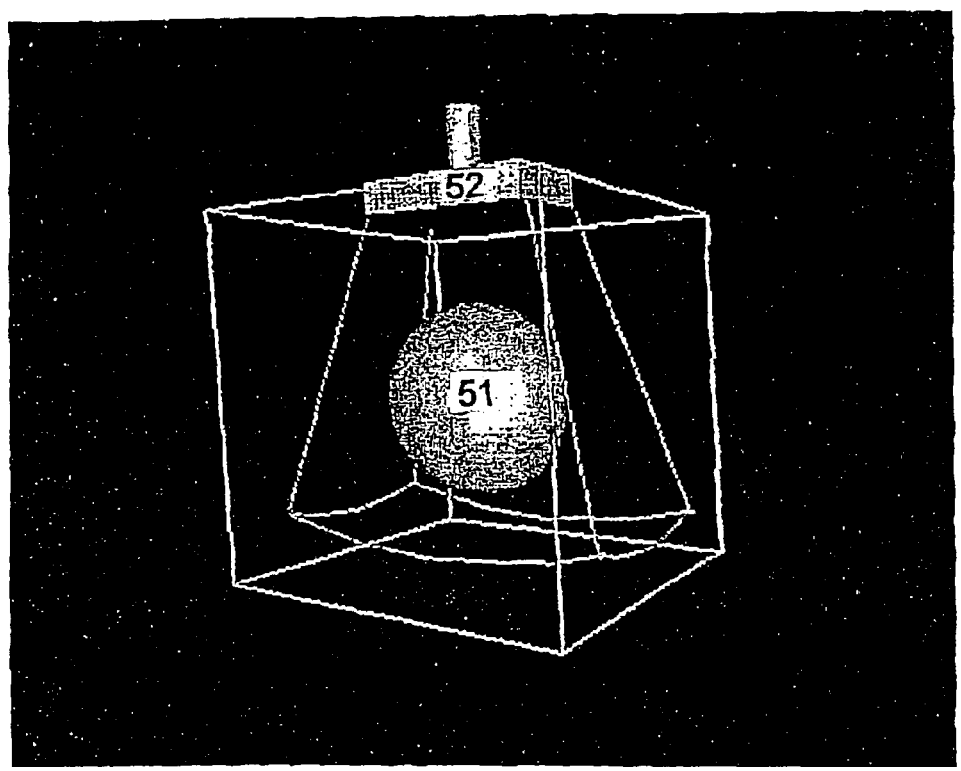
FIG. 7 illustrates embodiments of a two-dimensional transducer (which has several rows of elements) to interrogate a three-dimensional volume. In this approach, the transducer is held stationary, and the different axial/azimuthal planes are interrogated via electronic focusing.

For clarity, the interrogation of a two-dimensional plane with multiple pushing locations (the axial/azimuthal plane—see FIG. 5 where transducer array 32 is positioned over a target region represented as a cube containing a region of varying stiffness 31) has been described. In other embodiments this method is carried out in a manner that includes the interrogation of a three-dimensional volume. This is accomplished in a variety of ways. According to a first example illustrated in FIG. 6, where a transducer array 42 is positioned over a target region represented as a square containing a region of varying stiffness 41, and is translated from a first position as shown by 42 to a second position shown by 42', one can use the existing planar system, and translate the transducer in the elevation dimension to sequentially interrogate a series of planes comprising a three-dimensional volume. According to a second example illustrated in FIG. 7, where transducer array 52 is positioned over a target region represented as a square containing a region of varying stiffness 51, one can use a two-dimensional transducer array (i.e. one that has several rows of elements), and keep the transducer in one location, and steer the beam (represented as lines within the cube) to interrogate a three-dimensional sector of the target region.

When using the ultrasound transducer array to either generate the high intensity pushing pulses, or the displacement tracking pulses, a set of multiple elements may be used to generate each line. The set of elements that is used can either comprise all of the elements in the transducer array, or include only a subset of the elements. The specific elements that are active for each transmit pulse is dictated by the desired focal depth, resolution, and depth of field for each line. According to a particular embodiment, the pushing beams can be tightly focused, therefore a fairly large number of elements can be used to generate each pushing beam.

The spatial peak temporal average intensities required to generate detectable displacements in tissue vary depending upon the tissue acoustic and mechanical characteristics. They can be from 10 W/cm$^2$ to 1000 W/cm$^2$, with higher intensities being associated with better Signal-to-Noise-Ratios (SNRs). A trade-off exists, however, between increasing intensities and the potential for tissue heating, which should preferably be minimized in this method. The preferred intensities are thus in the 100 to 400 W/cm$^2$ range. These values are higher than those used for diagnostic imaging (0.72 W/cm$^2$), and lower than those used for HIFU (High Intensity Focused Ultrasound) imaging (1000

W/cm²). Given the short application time in a single location, (i.e. 15 milliseconds), the required intensities should not pose a significant risk to the patient.

In the method implementation described herein, the high intensity acoustic energy is applied by using a series of multiple, relatively short duty cycle pulses (i.e. 40 pulses, each 10 microseconds long, applied over a time period of 10 milliseconds). The method can also be accomplished by delivering the same amount of acoustic energy in a much shorter time period using a single long pulse (i.e. 1 pulse, 0.4 milliseconds long). An important issue is delivering the required amount of acoustic energy to the tissue to achieve a given displacement, which can be accomplished using any number of pulsing regimes. One preferred mode of implementation is to use a single, long pulse (i.e. 0.5 milliseconds), to achieve the initial displacement, and then to intersperse some of the shorter duty cycle (i.e. 10 microseconds) high intensity pulses with the tracking pulses to hold the tissue in its displaced location while tracking. This would reduce the amount of time required at each pushing location, and thus reduce the potential for tissue heating, while at the same time still achieving the desired tissue displacements. The use of a single, long pulse would, however, require additional system modifications. It may, for example, require the addition of heat sinking capabilities to the transducer, as well as modification of a standard power supply to allow the generation of longer pulses.

The displacement data from each pushing location is combined to form a single image. In order to achieve a uniform image, normalization may be useful. There are three features may benefit from normalization: 1) attenuation, 2) pushing function shape and non-uniformity, and 3) time of acquisition of tracking lines. Each of these features may be normalized out of the image, such that a Remote Palpation image of a homogeneous region of tissue will appear uniform.

While the method has been described in reference to lesion identification and characterization, it will also find use in any area where information about the varying mechanical properties of tissue or any other material subject to ultrasonography would be useful. Some examples include: 1) the characterization of arterial stiffness, which can be indicative of the degree of atherosclerotic disease, 2) the assessment of muscle tone, which is of importance in determining the course of treatment for female pelvic floor complications, and 3) assessing the stiffness of kidneys, which can be indicative of the viability of kidney transplants.

The foregoing is illustrative of the present invention, and is not to be construed as limiting thereof. The invention is described by the following claims, with equivalents of the claims to be included therein.

We claim:

1. An ultrasound method for detecting a region of altered stiffness contained within a medium, comprising the steps of:
   (a) delivering at least one pushing pulse from the ultrasound transducer array to the target region to displace a target region to a displaced position; then
   (b) delivering at least one first tracking pulse from the ultrasound transducer array to the target region to detect the displaced position of the target region;
   (c) delivering at least one second tracking pulse from the ultrasound transducer to the target region to detect a relaxed position of target regions; then
   (d) repeating steps (a) through (c) to provide a series of cycles, the at least one pushing pulse being delivered to different target regions during the series of cycles and to provide a plurality of displaced positions;
   (e) generating a plurality of displacement maps based on the relaxed position and the plurality of displaced positions; and then
   (f) combining the plurality of displacement maps to provide an image.

2. A method according to claim 1, wherein the step (d) of repeating steps (a) through (c) further comprises delivering the pushing pulses from different transducer elements in the ultrasound transducer array to different forcing regions during the cycles.

3. A method according to claim 1, wherein the step (d) of repeating further comprises delivering the at least one pushing pulse during the cycles from a plurality of ultrasound transducer elements of the ultrasound transducer array to different target regions during the cycles.

4. A method according to claim 1, wherein the ultrasound transducer array comprises a one dimensional ultrasound transducer array.

5. A method according to claim 1, wherein the ultrasound transducer array comprises a two dimensional ultrasound transducer array.

6. A method according to claim 1, wherein the region of altered stiffness comprises a region of greater stiffness relative to other regions indicated by a region of decreased displacement.

7. A method according to claim 6, wherein the medium comprises a biological tissue, and the region of greater stiffness is a tumor.

8. A method according to claim 7, wherein the tissue comprises breast tissue.

9. A method according to claim 6, wherein the medium comprises a blood vessel and the region of greater stiffness comprises a hardened blood vessel.

10. A method according to claim 6, wherein the medium comprises muscle tissue and the region of greater stiffness comprises muscle tissue with greater muscle tone relative to other regions.

11. A method according to claim 1, wherein the region of altered stiffness comprises a region of lesser stiffness relative to other regions indicated by a region of greater displacement within the image.

12. A method according to claim 1, further comprising the step of normalizing the displacement maps prior to the combining step.

13. A method according to claim 1, wherein the delivering step (c) is carried out while concurrently delivering at least one second pushing pulse to the target region to reduce a return of the target region from the displaced position to the initial position.

14. A method according to claim 1, wherein steps (a) through (c) are completed in about 50 milliseconds or less.

15. A method according to claim 1, further comprising the step of displaying the image.

16. A method according to claim 1, further comprising the steps of:
   generating a B-mode image of the two dimensional plane; and
   displaying the image superimposed on the B-mode image.

17. A method according to claim 1, further comprising the step of precompressing the target region prior to delivering the at least one pushing pulse.

18. A method according to claim 1, wherein the two-dimensional plane resides within a three-dimensional volume.

19. A method according to claim 1, wherein the image comprises a two-dimensional image.

20. A method according to claim 1, wherein the image comprises a three-dimensional image.

21. An ultrasound method comprising the steps of:
(a) delivering at least one first tracking pulse from an ultrasound transducer array to a target region within a medium to detect an initial position for the target region;
(b) delivering at least one pushing pulse from the ultrasound transducer array to the target region to displace the target region to a displaced position;
(c) delivering at least one second tracking pulse from the ultrasound transducer array to the target region to detect a displaced position of the target region; and
(d) repeating steps (a) through (c) to provide a series of cycles, the pushing pulses being delivered to different target regions during the series of cycles.

22. A method according to claim 21 wherein:
the step of delivering the at least one first tracking pulse comprises delivering the at least one first tracking pulse at a first intensity level; and
the step of delivering at least one pushing pulse comprises delivering the at least one pushing pulse at a second intensity level that is greater than the first intensity level.

23. A method according to claim 22 wherein the second intensity level is increased if a time of delivering the pushing pulse is decreased and the second intensity level is decreased if the time of delivering the pushing pulse is increased.

24. A method according to claim 22 wherein the step of delivering at least one second tracking pulse comprises delivering the at least one second tracking pulse at the first intensity level.

25. A method according to claim 22 wherein the second intensity level is a range between about 10.0 W/cm$^2$ and about 1000.0 W/cm$^2$.

26. A method according to claim 22 wherein the first intensity level is about 0.72 W/cm$^2$.

27. A method according to claim 23 wherein the step of delivering the at least one pushing pulse comprises delivering the at least one pushing pulse for about 0.5 milliseconds at about 1000.0 W/cm$^2$.

28. An ultrasound method comprising the steps of:
delivering a tracking pulse from an ultrasound transducer array to a target region within a medium to detect an initial position for the target region;
delivering a pushing pulse from the ultrasound transducer array to the target region to displace the target region to a displaced position; and
delivering a second tracking pulse from the ultrasound transducer array to the target region to detect the displaced position of the target region.

29. A method according to claim 28 wherein
the step of delivering the first tracking pulse comprises delivering the first tracking pulse at a first intensity level; and
the step of delivering a pushing pulse comprises delivering the pushing pulse at a second intensity level that is greater than the first intensity level.

30. A method according to claim 29 wherein:
the step of delivering a second tracking pulse comprises delivering the second tracking pulse at the first intensity level.

31. A method according to claim 29 wherein the second intensity level is a range between about 10.0 W/cm$^2$ and about 1000.0W/cm$^2$.

32. A method according to claim 29 wherein the first intensity level is about 0.72 W/cm$^2$.

33. A method according to claim 29 wherein the second intensity level is increased if a time of delivering the pushing pulse is decreased and the second intensity level is decreased if the time of delivering the pushing pulse is increased.

34. A method according to claim 33 wherein the step of delivering a pushing pulse comprises delivering the pushing pulse for about 0.5 milliseconds at about 1000.0 W/cm$^2$.

35. An ultrasound apparatus for detecting a region of altered stiffness contained within a medium, comprising:
(a) an ultrasound transducer array;
(b) first transmit means for delivering at least one first tracking pulse from an ultrasound transducer array to at least one target region within the medium to detect an initial position for the at least one target region;
(c) second transmit means for delivering at least one pushing pulse from the ultrasound transducer array to the at least one target region to displace the target region to a plurality of displaced positions;
(d) third transmit means for delivering at least one second tracking pulse from the ultrasound transducer array to the at least one target region to detect the plurality of displaced positions;
(e) control means associated with the first second and third transmit means for providing cycles of delivering pushing pulses to different target regions during the cycles;
(f) means for generating a plurality of displacement maps based on the initial position and the plurality of displaced positions; and
(g) means for combining the plurality of displacement maps to provide an image.

* * * * *